United States Patent [19]

Sakurai et al.

[11] Patent Number: 4,570,479
[45] Date of Patent: Feb. 18, 1986

[54] AIR-FUEL RATIO DETECTOR AND METHOD OF MEASURING AIR-FUEL RATIO

[75] Inventors: Shigenori Sakurai; Takashi Kamo; Tadayoshi Ikai, all of Aichi, Japan

[73] Assignee: Toyota Jidosha Kabushiki Kaisha, Toyota, Japan

[21] Appl. No.: 576,955

[22] Filed: Feb. 3, 1984

[30] Foreign Application Priority Data

Jul. 25, 1983 [JP] Japan ............... 58-135525

[51] Int. Cl.[4] .......................... G01M 15/00
[52] U.S. Cl. ......................... 73/116; 73/23; 204/412; 204/426
[58] Field of Search ............ 73/23, 116; 123/489; 204/412, 426

[56] References Cited

U.S. PATENT DOCUMENTS

| | | | |
|---|---|---|---|
| 4,051,006 | 9/1977 | Neti et al. | 204/412 X |
| 4,231,733 | 11/1980 | Hickam | 204/426 X |
| 4,487,680 | 12/1984 | Logothetis et al. | 204/412 X |

Primary Examiner—Jerry W. Myracle
Attorney, Agent, or Firm—Oblon, Fisher, Spivak, McClelland & Maier

[57] ABSTRACT

A detector and a measuring method for detecting an air-fuel ratio in an internal combustion engine or the like. The detector has a tubular body having a closed end, a solid electrolyte permeable to oxygen ions which divides the interior of the tubular body into a closed-end section and an open-end section, and electrodes mounted on opposite surfaces of the solid electrolyte. One pair of the electrodes on the opposite surfaces of the solid electrolyte is connected to a circuit for detecting an electromotive force, thus constituting an oxygen sensor. The other electrode pair is connected to a DC power supply, thus constituting an oxygen pump. The oxygen sensor detects the quantity of oxygen in a gas supplied through a gas dispersion member. The direction of flow and magnitude of and electric current in the oxygen pump are controlled on the basis of an output from the oxygen sensor for enabling the gas to have a stoichiometric air-fuel ratio.

9 Claims, 7 Drawing Figures

AIR-FUEL RATIO DETECTOR AND METHOD OF MEASURING AIR-FUEL RATIO

BACKGROUND OF THE INVENTION

1. Field of the Invention

The present invention relates to a detector for detecting an air-fuel ratio, or a ratio of air to fuel in an internal combustion engine or the like, and a method of measuring an air-fuel ratio.

2. Description of the Prior Art

It is currently known to detect oxygen density in an exhaust gas emitted from an internal combustion engine of an automobile or the like and control the amounts of air and fuel to be supplied to the internal combustion engine based on the detected oxygen density value, thereby reducing harmful components in the exhaust gas.

Air-fuel ratio detectors (oxygen sensors) presently available for internal combustion engines for automobiles for detecting oxygen densities operate on the principle of an oxygen concentration cell. This type of air-fuel ratio detector is capable of detecting a stoichiometric air-fuel ratio (A/F = 14.6) because of its characteristics. However, it cannot detect air-fuel ratios in other ranges, that is, a lean range in which the air-fuel ratio is higher than the stoichiometric air-fuel ratio or a rich range in which the air-fuel ratio is lower than the stoichiometric air-fuel ratio. When a voltage is applied between gas-permeable thin-film electrodes attached to a solid electrolyte cell permeable to oxygen ions, oxygen ions pass through the cell from the cathode to the anode, and with the oxygen ions flows an electric current between the electrodes. If the quantity of oxygen ions which are going to pass through the cell is limited as by forming a porous ceramic coating layer on the cathode, then limited-current characteristics appear in which the current is not increased beyond a certain value even when an applied voltage is increased. Utilizing such phenomenon, there has been developed a limited-current oxygen sensor for detecting oxygen densities with a view to detecting air-fuel ratios in the lean range. Since the limited-current oxygen sensor is capable of detecting air-fuel ratios in the lean range only, such is called a "lean sensor", and is almost incapable of detecting air-fuel ratios in the rich range.

While an automobile is running under ordinary conditions, it is preferable to be driven in the lean range in which an air-fuel mixture is lean. When the engine is required to produce a higher power output such as during travel up a slope, the automobile is preferably driven in the rich range. Therefore, there has been a demand for a detector capable of detecting an air-fuel ratio in the rich to the lean range.

SUMMARY OF THE INVENTION

It is an object of the present invention to provide an air-fuel ratio detector capable of detecting, by itself, an air-fuel ratio in the rich to the lean range.

Another object of the present invention is to facilitate the manufacture and handling of an air-fuel ratio detector by constructing such detector of one solid electrolyte element.

Still another object of the present invention is to enable more efficient engine control by causing an automobile, for example, to run under normal conditions at air-fuel ratios in the lean range and to produce a higher power output as when running up a slope at air-fuel ratios in the rich range.

Still another object of the present invention is to improve the combustion efficiency and fuel economy of combustion furnaces as well as engines.

A still further object of the present invention is to provide a method of measuring air-fuel ratios in the rich to lean range.

The above objects can be achieved according to the present invention by an air-fuel ratio detector comprising a tubular body, a pair of partition members hermetically contacting an inner peripheral surface of the tubular body transversely of an axis of the tubular body, one of the partition members being composed of solid electrolyte permeable to oxygen ions, gas dispersion means disposed in the other partition member or in the tubular body between the other partition member and the solid electrolyte, two pairs of gas-permeable thin-film electrodes mounted respectively on opposite sides of the solid electrolyte, and one pair of the electrodes on the opposite sides of the solid electrolyte being connected to a circuit for detecting an electromotive force, and the other pair of electrodes on the opposite sides of the solid electrolyte being connected to a DC power supply.

The tubular body may consist of various materials, but should preferably be of an inorganic material such as, for example, thermally resistant ceramics. the tubular body has a closed end having a gas dispersion hole or gas dispersion layer. The gas dispersion hole may be formed in an ordinary fashion, for example, by applying a laser beam to the tubular body formed of ceramic material, or by previously placing strings or other soluble materials in a mass of raw ceramics and then sintering the ceramics mass. The gas dispersion layer may be formed by joining a ceramic filter to an opening in the tubular body or fabricating a porous ceramic coating layer on a coarse porous ceramic body with plasma sparying.

The gas dispersion hole or layer may be positioned in a side wall of the tubular body near the closed end thereof. The tubular body may be in the shape of a cylinder or a parallelpiped.

When the detector is not used in a high-temperature atmosphere, the solid electrolyte is heated by heating means in the tubular body. The heating means may comprise a heater consisting of a Nichrome wire coiled around the tubular body, or preferably a heater embedded in the tubular body so that the latter will act as a ceramic heater. The heater is positioned in the vicinity of the solid electrolyte.

The solid electrolyte permeable to oxygen ions may be of the type which is employed in an air-fuel ratio detector or oxygen sensor of the kind described hereinafter. That is, where the solid electrolyte is in the form of a flat plate comprising zirconium oxide with yttrium oxide added.

The electrodes mounted on the surfaces of the solid electrolyte are in the form of air-permeable thin films formed of platinum in an ordinary manner. Two pairs of electrodes are provided and mounted on both sides of the plate-like solid electrolyte in such a manner that opposite electrodes form a pair. The electrodes in each pair are coextensive with each other on opposite surfaces of the solid electrolyte.

One of the two pairs of the electrodes is employed as an oxygen sensor of the oxygen concentration cell type. A voltage is applied to the other pair of electrodes to cause oxygen ions to pass through the solid electrolyte, thus being used as an oxygen pump.

As described above, the oxygen sensor of the oxygen concentration cell type fails to detect air-fuel ratios other than a stoichiometric air-fuel ratio, though it can detect the stoichiometric air-fuel ratio and values close thereto. According to the present invention, the other pair of electrodes is energized to supply oxygen from one electrode (cathode) to the other (anode) for providing an atmosphere of the stoichiometric air-fuel ratio. More specifically, when the gas to be inspected is in a rich condition, oxygen is fed into the gas by the oxygen pump to cause the gas to have the stoichiometric air-fuel ratio. Conversely, when the gas to be inspected is in a lean condition, oxygen is removed from the gas by the oxygen pump.

The oxygen flows through the solid electrolyte in a direction opposite to that in which an electric current flows therethrough. The electric current is increased or reduced in magnitude or its direction of flow is changed on the basis of the output from the oxygen sensor dependent on whether the gas is in the lean or rich condition. Since the quantity of oxygen flowing through the solid electrolyte is proportional to the electric current flowing therethrough, the air-fuel ratio of the gas to be inspected can be detected from the magnitude of the electric current.

The above and other objects, features and advantages of the present invention will become more apparent from the following description when taken in conjunction with the accompanying drawings in which preferred embodiments of the present invention are shown by way of illustrative example.

DETAILED DESCRIPTION OF THE PREFERRED EMBODIMENTS

Figure 1:
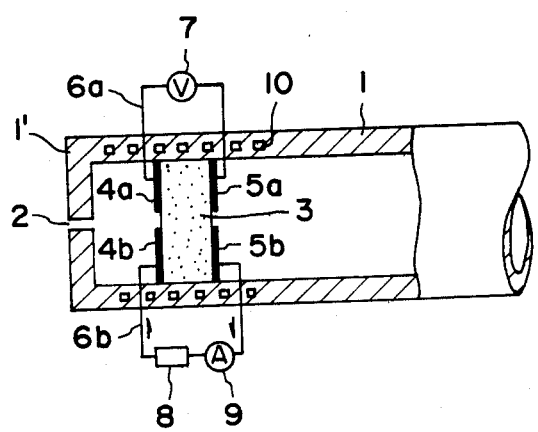
FIG. 1 is a fragmentary cross-sectional views of an air-fuel ratio detector according to a first embodiment of the present invention.

FIG. 1 shows in cross section an air-fuel ratio detector according to a representative embodiment (first embodiment) of the present invention. The air-fuel ratio detector comprises a cylindrical tubular body 1 made of ceramic material having a gas dispersion hole 2 defined in a closed end 1' of the body 1. The cylindrical tubular body 1 accommodates therein a disk-shaped solid electrolyte 3 supporting electrodes 4a, 4b, 5a, 5b thereon.

Figure 2:
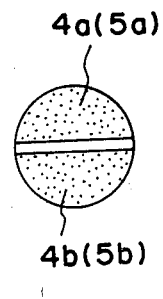
FIG. 2 is a plan view of electrodes formed on a solid electrolyte.

The electrodes 4a, 4b, 5a, 5b are of a semicircular shape and attached to the surfaces of both sides of the solid electrolyte 3, as illustrated in FIG. 2.

Electrodes 4a, 4b disposed on one surface of the solid electrolyte 3 face the gas dispersion hole 2 so that a gas to be inspected such as an exhaust gas will be brought into contact with the electrodes 4a, 4b. The electrodes 5a, 5b disposed on the opposite surface of the solid electrolyte 3 are kept in communication with atmosphere. At least the electrodes 4a, 4b which will contact the gas should consist of catalytically active electrodes.

As shown in FIG. 1, the electrodes 4a, 5a are paired and connected by lead wires 6a to a voltage measuring device 7, thus constituting an oxygen sensor. The other electrodes 4b, 5b are also paired and connected by lead wires 6b to a DC power supply 8 and a current measuring device 9, thus constituting an oxygen pump.

A heater 10 is disposed in the cylindrical tubular body 1 as is the case with an ordinary ceramic heater. The heater 10 is connected by lead wires (not shown) to a power supply. When necessary to meet characteristic requirements of the detector, the heater 10 is energized to heat the air-fuel ratio detector. For example, the heater 10 is energized when the detector does not reach a required operating temperature at the time of detecting an exhaust gas of low temperatures resulting from combustion of a lean air-fuel mixture.

The air-fuel ratio detector thus constructed operates as follows: The quantity of oxygen in a gas to be inspected which has entered into the detector through the gas dispersion hole 2 is detected by the oxygen sensor, and the direction of flow and magnitude of an electric current supplied to the oxygen pump are controlled on the basis of an output from the oxygen sensor for bringing the air-fuel ratio of the gas in the space between the gas dispersion hole 2 and the electrodes 4a, 4b into conformity with a stoichiometric air-fuel ratio. To this end, the DC power supply 8 is arranged to increase or reduce the current and vary its polarity based on the output from the oxygen sensor.

Where the gas is in a rich condition and its air-fuel ratio is to be equalized to the stoichiometric air-fuel ratio, it is necessary to add oxygen to the gas. By passing an electric current from the electrode 4b to the electrode 5b, oxygen flows in a direction opposite to that of the current, that is, the current flows from atmosphere to the gas. When the oxygen is supplied in an optimum quantity, the gas in the space between the gas dispersion hole 2 and the electrodes 4a, 4b has a stoichiometric air-fuel ratio. Where the gas is in a lean condition, the electric current passes in the opposite direction.

Figure 3:
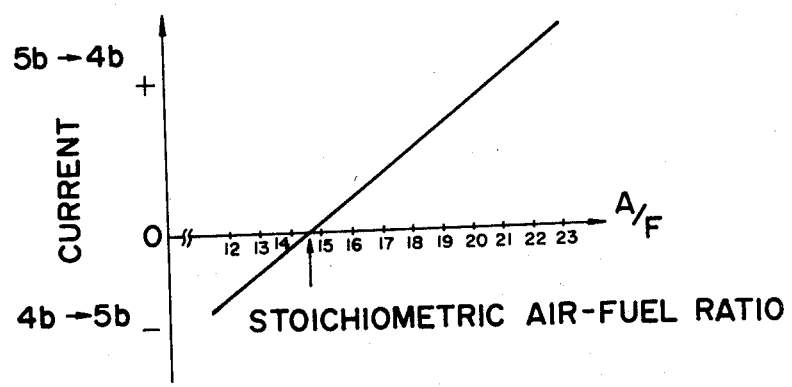
FIG. 3 is a graph showing the relationship between a stoichiometric air-fuel ratio and an output electric current.

Since the quantity of oxygen flowing through the solid electrolyte 3 is proportional to the electric current, the relationship between the stoichiometric air-fuel ratio of the gas present outside and inside the detector or the gas dispersion hole 2 and the value of the electric current at which the above mentioned gases become a stoichiometric air-fuel ratio is shown in FIG. 3. Therefore, the air-fuel ratio of the gas can be detected if the value of the electric current flowing through the oxygen pump is known. In FIG. 3, the direction in which the electric current flows from the electrode 5b to the electrode 4b is assumed to be positive.

Air-fuel ratio detectors according to other embodiments are illustrated in FIGS. 4 through 7.

Figure 4:
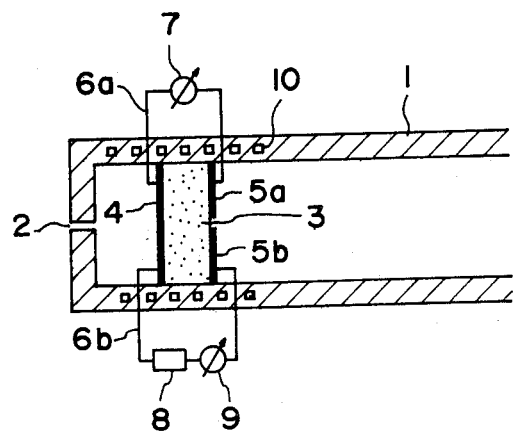
FIGS. 4 through 7 are fragmentary cross-sectional views of air-fuel ratio detectors according to other embodiments of the present invention.

According to a second embodiment shown in FIG. 4, the solid electrolyte 3 is provided by a common electrode 4, instead of the separate electrodes, 4a, 4b in the first embodiment, on the surface facing the gas to be inspected. The other construction of the air-fuel detector is the same as that of the first embodiment.

Figure 5:
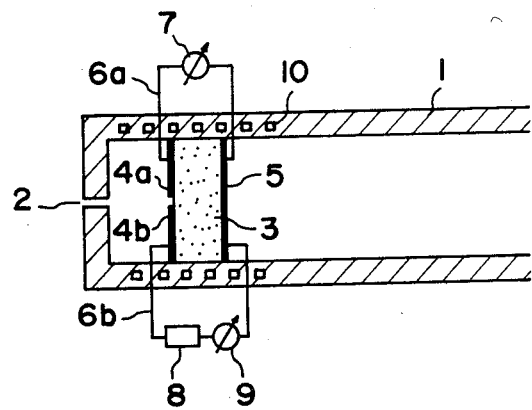

FIG. 5 shows an air-fuel ratio detector according to a third embodiment in which a common electrode 5 is disposed in communication with atmosphere.

Figure 6:
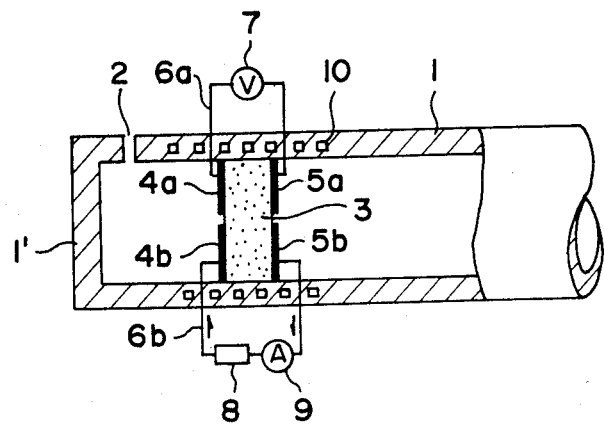

An air-fuel ratio detector according to a fourth embodiment illustrated in FIG. 6 has a gas dispersion hole 2 defined in a side wall of a tubular body 1.

Figure 7:
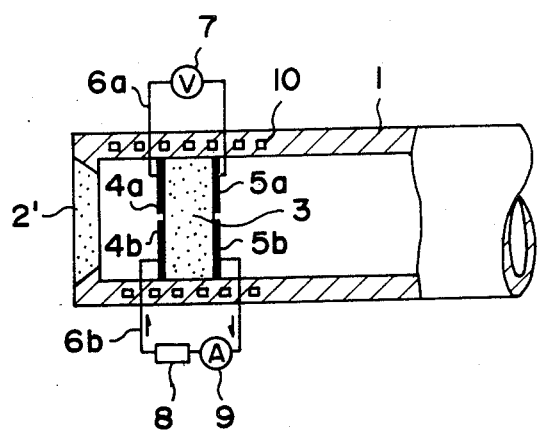

As shown in FIG. 7, an air-fuel ratio detector according to a fifth embodiment has a gas dispersion layer, rather than a gas dispersion hole, comprising a ceramic filter 2' disposed in a closed end of a tubular body 1.

Although certain preferred embodiments have been shown and described, it should be understood that many changes and modifications may be made therein without departing from the scope of the appended claims.

What is claimed as new and desired to be secured by Letters Patent of the United States is:

1. An air-fuel ratio detector for detecting oxygen density in exhaust gas emitted from an engine, comprising:
   a DC power supply;
   a circuit for detecting an electromotive force;
   a tubular body;
   first and second partition members hermetically contacting an inner peripheral surface of said tubular body transversely of an axis of said tubular body wherein said first partition member further comprises a solid electrolyte permeable to oxygen ions;
   gas dispersion means operatively associated with said solid electrolyte for communicating said gas to said solid electrolyte;
   first and second pairs of spaced apart gas-permeable thin-film electrodes separately mounted on opposite sides of said solid electrolyte, said first pair of electrodes being connected to said circuit for detecting an electromotive force and said second pair of electrodes being connected to said DC power supply.

2. An air-fuel ratio detector set forth in claim 1, wherein said gas dispersion means further comprises a gas dispersion hole defined in a side wall portion of said tubular body.

3. An air-fuel ratio detector accordingly to claim 1, wherein said gas dispersion means further comprises a gas dispersion hole formed in said second partition member.

4. An air-fuel ratio detector according to claim 1, wherein said gas dispersion means further comprises a gas dispersion layer disposed in said second partition member.

5. An air-fuel ratio detector for detecting oxygen density in an exhaust gas emitted from an engine, comprising:
   a DC power supply;
   a circuit for detecting an electromotive force;
   a tubular body;
   first and second partition members hermetically contacting an inner peripheral surface of said tubular body transversely of an axis of said tubular body wherein said first partition member further comprises a solid electrolyte permeable to oxygen ions;
   gas dispersion means operatively associated with said solid electrolyte for communicating said gas to said solid electrolyte; and
   a pair of spaced apart gas-permeable thin-film electrodes separately mounted on one side of said electrolyte, and a single electrode mounted on an opposite side of said solid electrolyte, one of said pair of electrodes and said single electrode being connected to said circuit for detecting an electromotive force and the other one of said pair of electrodes and said single electrode being connected to said DC power supply.

6. An air-fuel ratio detector as set forth in claim 5, wherein said gas dispenser means further comprises a gas dispersion hole defined in a side wall portion of said tubular body.

7. An air-fuel ratio detector according to claim 5, wherein said gas dispersion means further comprises a gas dispersion hole formed in said second partition member.

8. An air-fuel ratio detector as set forth in claim 5, wherein said gas dispersion means further comprises a gas dispersion layer disposed in said second partition member.

9. A method of measuring an air-fuel ratio to detect oxygen density and exhaust gas emitted from an engine, which comprises:
   positioning a solid electrolyte permeable to oxygen ions in a tubular body so as to form a partition of a closed measuring chamber within said tubular body and into which a gas to be inspected flows;
   mounting a first pair of electrodes and a second pair of electrodes stretching over both surfaces of said solid electrolyte, respectively;
   connecting said first pair of electrodes to a DC power supply and said second electrodes to a voltage measuring device; and
   controlling the direction of flow and magnitude of electric current flowing between one pair of electrodes so as to enable the gas in said measuring chamber to have a stoichiometric air-fuel ratio on the basis of the output from the remaining pair of electrodes.

* * * * *